(12) United States Patent
Pesetski et al.

(10) Patent No.: US 8,548,415 B2
(45) Date of Patent: *Oct. 1, 2013

(54) CARBON NANOTUBE DEVICES AND METHOD OF FABRICATING THE SAME

(75) Inventors: Aaron A. Pesetski, Gambrills, MD (US);
Hong Zhang, Gambrills, MD (US);
John Xavier Przybysz, Severna Park, MD (US); John Douglas Adam, Millersville, MD (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 1726 days.

This patent is subject to a terminal disclaimer.

(21) Appl. No.: 11/889,350

(22) Filed: Aug. 10, 2007

(65) Prior Publication Data
US 2012/0182178 A1 Jul. 19, 2012

Related U.S. Application Data

(63) Continuation-in-part of application No. 11/012,864, filed on Dec. 16, 2004, now Pat. No. 7,359,694.

(51) Int. Cl.
*H04B 1/26* (2006.01)
*H04B 1/28* (2006.01)

(52) U.S. Cl.
CPC ........................ *H04B 1/28* (2013.01)
USPC ....................................... 455/323

(58) Field of Classification Search
CPC ........................................ H04B 1/28
USPC ............. 455/323, 324, 325, 326, 327, 330, 455/333, 334; 327/113, 355, 357, 358; 257/300, 399
See application file for complete search history.

(56) References Cited

U.S. PATENT DOCUMENTS

| | | | |
|---|---|---|---|
| 6,901,249 B1 * | 5/2005 | Kobayashi | 455/333 |
| 7,734,271 B2 * | 6/2010 | Pepper et al. | 455/313 |
| 2001/0023968 A1 * | 9/2001 | Smith et al. | 257/399 |
| 2002/0014999 A1 | 2/2002 | Crowley | |
| 2005/0056877 A1 * | 3/2005 | Rueckes et al. | 257/300 |
| 2005/0282515 A1 | 12/2005 | Bertin | |
| 2006/0261433 A1 | 11/2006 | Manohara et al. | |
| 2007/0281657 A1 | 12/2007 | Brommer et al. | |

FOREIGN PATENT DOCUMENTS

| | | |
|---|---|---|
| EP | 0917283 A2 | 5/1999 |
| JP | 2002076324 | 3/2002 |
| WO | 0103208 A1 | 1/2001 |
| WO | 2004030043 A2 | 4/2004 |

OTHER PUBLICATIONS

Peter H. Siegel, Terahertz Technology, IEEE Transactions on Microwave Theory and Technique, Mar. 2002, p. 910-928, vol. 50, No. 3.
Chin Li Cheung, Andrea Kurtz, Hongkun Park, and Charles M. Lieber, Diameter-Controlled Synthesis of Carbon Nanotubes, J. Phys. Chem. B, Feb. 16, 2002, p. 2429-2433, 106, Web.

(Continued)

*Primary Examiner* — Thanh Le
(74) *Attorney, Agent, or Firm* — Rothwell, Figg, Ernst & Manbeck, P.C.

(57) ABSTRACT

An imaging system includes an RF source, a focal plane array and device for focusing the RF signal from the RF source. The focal plane array includes a plurality of carbon nanotube mixers for capturing RF signals and down-converting the signals to a selected bandwidth and output an output signal. The device focuses the RF signal output from said RF source onto the focal plane array.

18 Claims, 20 Drawing Sheets

To avoid resistive losses, the LO will be broadcast to the focal plane array as vertically polarized radiation.

(56) References Cited

OTHER PUBLICATIONS

Marc Bockrath, J. Hone, A . Zettl, and Paul L. McEuen, Chemical Doping of Individual Semiconducting Carbon-Nanotube Ropes; Rapid Communications Physical Review B, R10 606-R10-608, Apr. 15, 2000, vol. 61, No. 16, The American Physical Society.

V. Derycke, R. Martel, J. Appenzeller and Ph Avouris, Carbon Nanotube Inter- and Intramolecular Logic Gates, Nano Letters, Aug. 16, 2001, p. A-D, vol. 0, No. 0.

Chongwu Zhou, Jing Kong, Erhan Yenilmez, Hongjie Dai, Modulated Chemical Doping of Individual Carbon Nanotubes, Science Magazine, Nov. 24, 2000, p. 1552-1555, www.sciencemag.org.

R. S. Lee, H. J. Kim, J. E. Fischer, A. Thess and R. E. Smalley, Conductivity Enhancement in Single-walled Carbon Nanotube Bundles Doped with K and Br, Nature, Jul. 17, 1997, p. 255-257, vol. 388.

T. Dükkop, S. A. Getty, Enrique Cobas, and M. S. Fuhrer, Extraordinary Mobility in Semiconducting Carbon Nanotubes, Nano Letters, Dec. 3, 2003, p. 35-39, vol. 4, No. 1, 2004 American Chemical Society.

All Javey, Jing Guo, Qian Wang, Mark Lundstrom and Hongjie Dai, Ballistic Carbon Nanotube Field-effect Transistors, Nature, Aug. 2003, p. 654-657, vol. 424, www.nature.com/nature.

Y. Yaish, J.-Y. Park, S. Rosenblatt, V. Sazonova, M. Brink, and P. L. McEuen, Electrical Nanoprobing of Semiconducting Carbon Nanotubes Using an Atomic Force Microscope, Unrelated, Cornell University, 2002, p. 1-4.

David H. Cobden, Marc Bockrath, and Paul L. McEuen, Spin Splitting and Even-odd Effects in Carbon Nanotubes, Physical Review Letters, Jul. 20, 1998, p. 681-684, vol. 81, No. 3, The American Physical Society.

B. Nabet, E. Gallo, M. Freitag, A. T. Johnson, and X. Chen, Local Variation of Metal-semiconducting Carbon Nanotube Contact Barrier Height, IEEE-Nano 2002, Aug. 28, 2002, p. 435-438, IEEE.

A. S. Vedeneev, J. Li, C. Papadopoulos, A. Rakitin, A. J. Bennett, H. W. Chik and J. M. Xu, Molecular-scale Rectifying Diodes Based on Y-junction Carbon Nanotubes, IEEE, 1999, p. 9.5.1-9.5.3.

Phaedon Avouris, Joerg Appenzeller, Richard Martel, and Shalom J. Wind, Carbon Nanotube Electronics, Invited Paper, Nov. 11, 2003, p. 1772-1784, vol. 91, No. 11, Proceedings of the IEEE.

Donald D. King, Passive Detective, p. 1-34, Phillips Laboratories.

I. Mehdi, T.H. Lee, D.A. Humphrey, S.C. Martin, R.J. Dengler, J. E. Oswald, A. Pease, R. P. Smith and P. H. Seigel, 600 Ghz Planar-Schottky-Diode Subharmonic Waveguide Mixers, Jet Propulsion Laboratory California Institute of Technology, IEEE, Jun. 1996, p. 377-380, IEEE MTT-S Digest.

N. R. Franklin and H. Dai, An Enhanced CVD Approach to Extensive Nanotube Networks with Directionality, Advanced Materials, Mar. 28, 2000, p. 890-894, vol. 12, No. 12.

Shaoming Huang, Xinyu Cai and Jie Liu, Growth of Millimeter-long and Horizontally Aligned Single-walled Carbon Nanotubes on Flat Substrates, J. Am. Chem. Soc., Apr. 22, 2003, p. 5636-5637, 125.

Chin Li Cheung, Andrea Kurtz, Hongkun Park, and Charles M. Lieber, Diameter-Controlled Synthesis of Carbon Nanotubes, J. Phys. Chem. B, 2002, p. 2429-2433, vol. 106, American Chemical Society.

Yiming Li, Woong Kim, Yuegang Zhang, Marco Rolandi, Dunwei Wang and Hongjie Dai, Growth of Single-Walled Carbon Nanotubes from Discrete Catalytic Nanoparticles of Various Sizes, J. Phys. Chem. B., 2001, p. 11424-11431, vol. 105, American Chemical Society.

Lei An, Jessica M. Owens, Laurie E. McNeil, and Jie Liu, Synthesis of Nearly Uniform Single-Walled Carbon Nanotubes Using Identical Metal-Containing Molecular Nanoclusters as Catalysts, Jun. 27, 2002, p. 1-2, 6.

Philip G. Collins, Michael S. Arnold, and Phaedon Avouris, Engineering Carbon Nanotubes and Nanotube Circuits Using Electrical Breakdown, Apr. 27, 2001, p. 706-709, vol. 292, Science, www.sciencemag.org.

Paul L. McEuen, Michael S. Fuhrer, and Hongkun Park, Single-Walled Carbon Nanotube Electronics, Mar. 2002, p. 78-85, vol. 1, No. 1, IEEE Transactions on Nanotechnology.

P.-E. Roche, M. Kociak, M. Ferrier, S. Guéron, A. Kasumov, B. Reulet, and H. Bouchiat, Shot Noise in Carbon Nanotubes, Invited Papers, 2003, p. 104-115, vol. 5115, Proceedings of SPIE, Noise and Information in Nanoelectronics, Sensors, and Standards.

D. S. Bethune, C. H. Klang, M. S. de Vries, G. Gorman, R. Savoy, J. Vazquez and R. Beyers, Cobalt-Catalysed Growth of Carbon Nanotubes with Single-Atomic-Layer Walls, Nature, Jun. 17, 1993, p. 605-607, vol. 363, Letters to Nature.

C. Journet, W. K. Maser, P. Bernier, A. Loiseau, M. Lamy De La Chapello, S. Lefrants, P. Denlard, R. Lee and J. E. Fischer, Large-scale production of single-walled carbon nanotubes by the electric-arc technique, Nautre, Aug. 21, 1997, p. 756-757, vol. 388, Letters of Nature.

Brinda B. Lakshmi and Charles R. Martin, Enantioseparation Using Apoenzymes Immobilized in a Porous Polymeric Membrane, Nature, Aug. 21, 1997, p. 758, vol. 388, Letters of Nature.

Andreas Thess, Roland Lee, Pavel Nikolaev, Hongjie Dai, Pierre Petit, Jerome Robert, Chunhui Xu, Young Hee Lee, Seong Gon Kim, Andrew G. Rinzler, Daniel T. Colbert, Gustavo E. Scuseria, David Tománek, John E. Fischer, and Richard E. Smalley, Chrystalline Ropes of Metallic Carbon Nanotubes, Science, Jul. 26, 1996, p. 483-487, vol. 273.

Noise Analysis, Diode Mixer Theory, p. 135-142, vol. 135.

Millimeter Frequency Conversion Using Au-n-Type GaAs Schottky Barrier Epitaxial Diodes with a Novel Contacting Technique, Manuscript, Oct. 22, 1965, p. 2130-2131.

Avouris, P. et al., "Carbon Nanotube Electronics," International Electron Devices Meeting 2002. Technical Digest, pp. 281-284.

Kawazoe, Yoshiyuki, "How Ab initio Computer Simulation can Predict Materials Properties before Experiment," Intelligent Processing and Manufacturing of Materials, 1999, pp. 355-359.

Office Action for JP2007-546943 dated Dec. 25, 2012, 5 pages.

* cited by examiner

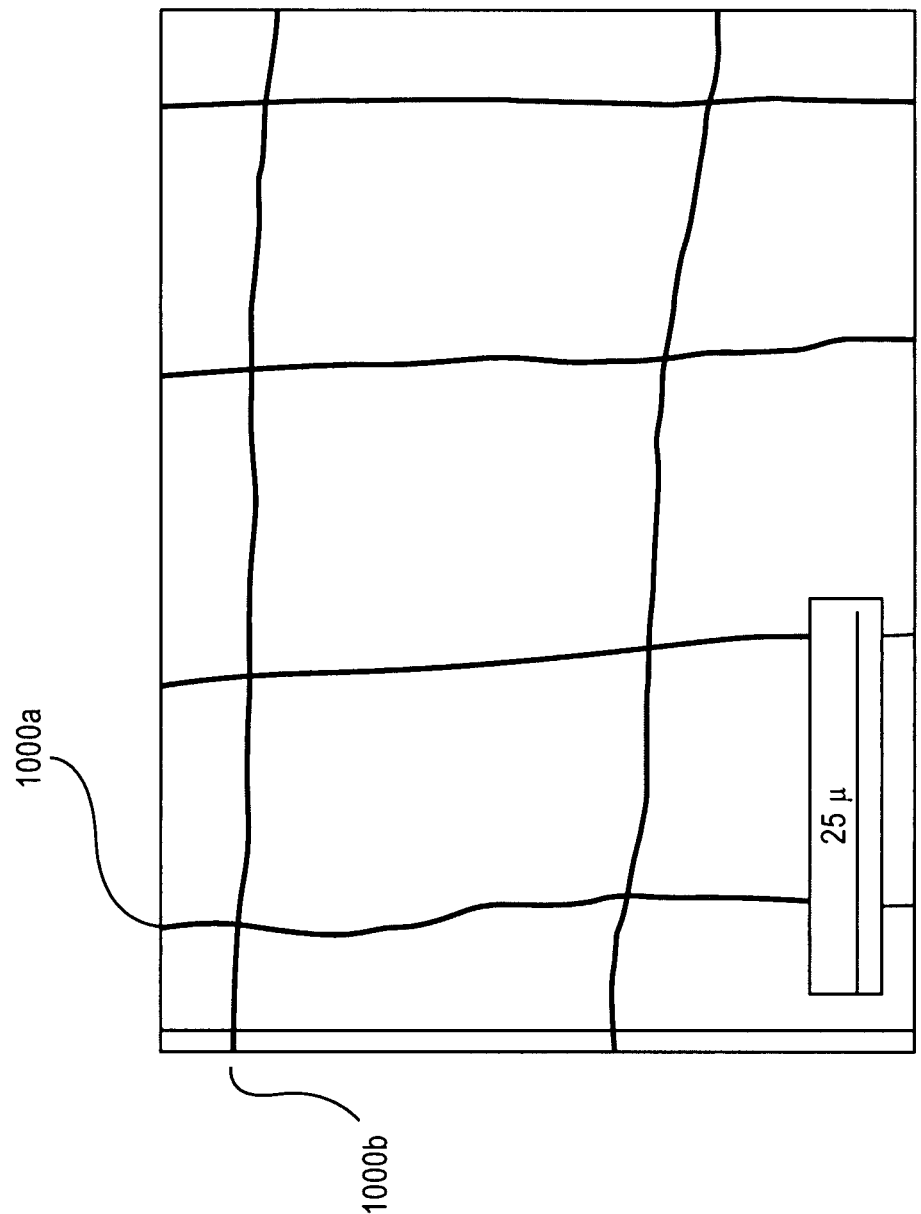

Figure III.D.25 To avoid resistive losses, the LO will be broadcast to the focal plane array as vertically polarized radiation.

CARBON NANOTUBE DEVICES AND METHOD OF FABRICATING THE SAME

RELATED APPLICATION DATA

This application is a continuation-in-part of and claims the benefit of priority to U.S. patent application Ser. No. 11/012,864, filed on Dec. 16, 2004, the entire contents of which are hereby incorporated by reference.

BACKGROUND OF THE INVENTION

1. Field of the Invention

The present invention relates generally to radio frequency (RF) devices, and more particularly, the present invention relates to high frequency detectors, mixers and scanners that utilize carbon nanotube technology.

2. Description of the Related Art

Carbon nanotubes were discovered in the early 1990s as a product of arc-evaporation synthesis of fullerenes. Scientists have since determined that carbon nanotubes have extraordinary physical characteristics, and their potential use in many different applications has attracted much attention. For example, single-wall carbon nanotubes have high-current density and low capacitance characteristics. However, no commercially viable electronic applications for nanotube technologies have been available until very recently.

There has been much interest in the semi-conducting properties of carbon nanotubes. The small size of carbon nanotube (CNT) devices (~1 nm) results in an ultra-low capacitance (~1 $aF=10^{-18}$ F) which, in turn, allows CNT devices to operate at speeds well into the terahertz frequencies.

Thus, there is a need for new and improved products based upon carbon nanotube technology.

SUMMARY OF THE INVENTION

According to embodiments of the present invention, novel systems and methods utilizing nanotube diode technology are provided. According to one embodiment of the present invention, a radio frequency (RF) mixer is provided that includes a RF input and at least two carbon nanotube diodes coupled with said RF input.

According to another embodiment of the present invention, a RF mixer includes CNT diodes or FETs formed from arrays of CNTs. Each carbon nanotube includes a p-n junction. The mixer also includes a RF input coupled to each of the diodes or FETs and a local oscillator input coupled with each of the diodes or FETs.

According to another embodiment of the present invention, a focal plane is provided that includes a carbon nanotube mixer.

Further applications and advantages of various embodiments of the present invention are discussed below with reference to the drawing figures.

BRIEF DESCRIPTION OF THE DRAWINGS

FIG. 10 is an image of crossed nanotubes grown on a substrate;

DETAILED DESCRIPTION OF THE PREFERRED EMBODIMENTS

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

Carbon nanotubes may be fabricated by a variety of methods. The most significant type of carbon nanotube is the single walled nanotube (SWNT). SWNTs can currently be grown up to 10 mm in length and can have either metallic or semiconductor characteristics. That is, depending on orientation of a carbon nanotube's crystal walls, carbon nanotubes may take on metallic characteristics or semiconductor characteristics. Carbon nanotubes (CNT) are referenced throughout this document as either metallic CNTs or semiconductor CNTs to reflect their characteristics.

Semiconductor CNTs may be selectively doped to form p-n junctions. One process for doping a CNT is called dip-pen nanolithography. In this process, a dopant is precisely sprayed ("painted") onto a nanotube with an Atomic Force Microwave (AFM) probe to form a p-n junction. An alternate method is to selectively deposit the dopant using standard lithography techniques.

Figure 14:
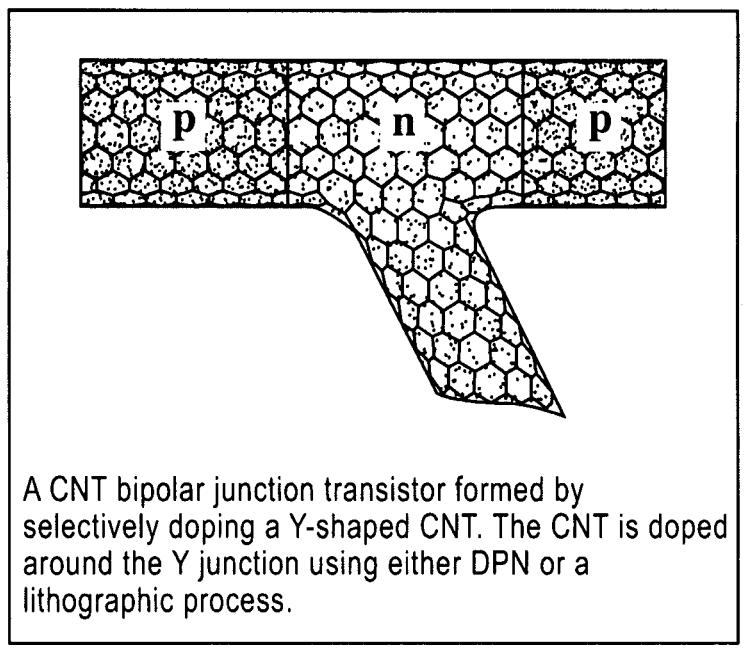
FIG. 14 depicts a CNT bipolar junction transistor (BJT) formed by selective doping a Y-shaped CNT.

Referring to FIG. 14, a CNT bipolar junction transistor (BJT) can be formed by selective doping a Y-shaped CNT. The CNT can be doped around the Y junction using either DPN or lithographic processes.

Figure 7:
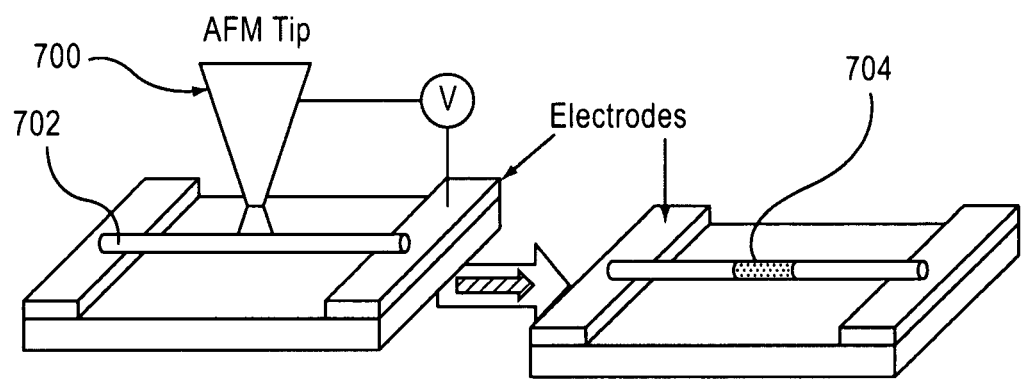
FIG. 7 is a diagram illustrating a method of doping a carbon nanotube.

FIG. 7 shows a carbon nanotube being selectively doped through dip-pen nanolithography. The AFM probe tip 700 is dipped in an electron donor, such as a chemical solution of aniline and polyethaline imide (PEI) or diazonium salts. The AFM 700 is then used to precisely paint carbon nanotube 702 in a selected region to change the selected region of the CNT from p-type to n-type, and as a result, creates the p-n junctions 704.

Doped CNTs have extremely good characteristics for use in RF devices. The capacitance of a single CNT having a p-n junction has been calculated to be 1 aF ($10^{-18}$ F). However, the impedance of a single nanotube can be too high to use at THz (Terahertz) frequencies, so diodes are preferably built from an array of doped nanotubes. Preferably at least ten nanotubes are utilized per diode, and more preferably, at least 100 nanotubes are used (using about 100 CNTs will reduce the diode impedance of 50-2000, which is sufficiently low enough to permit coupling with THz frequency circuits).

CNT's can be used to form Schottky junctions in addition to p-n junctions. Schottky barriers can be formed by using metals with different work functions to form the contacts at the ends of a CNT. As with p-n junction diodes, the resistance of a Schottky diode made from a single CNT will be too high to couple to RF or THz circuits. It is also possible to fabricate a Schottky diode with sufficiently low impedance to allow coupling to RF and THz circuits by using an array of CNTs to form a single diode.

Figure 8:
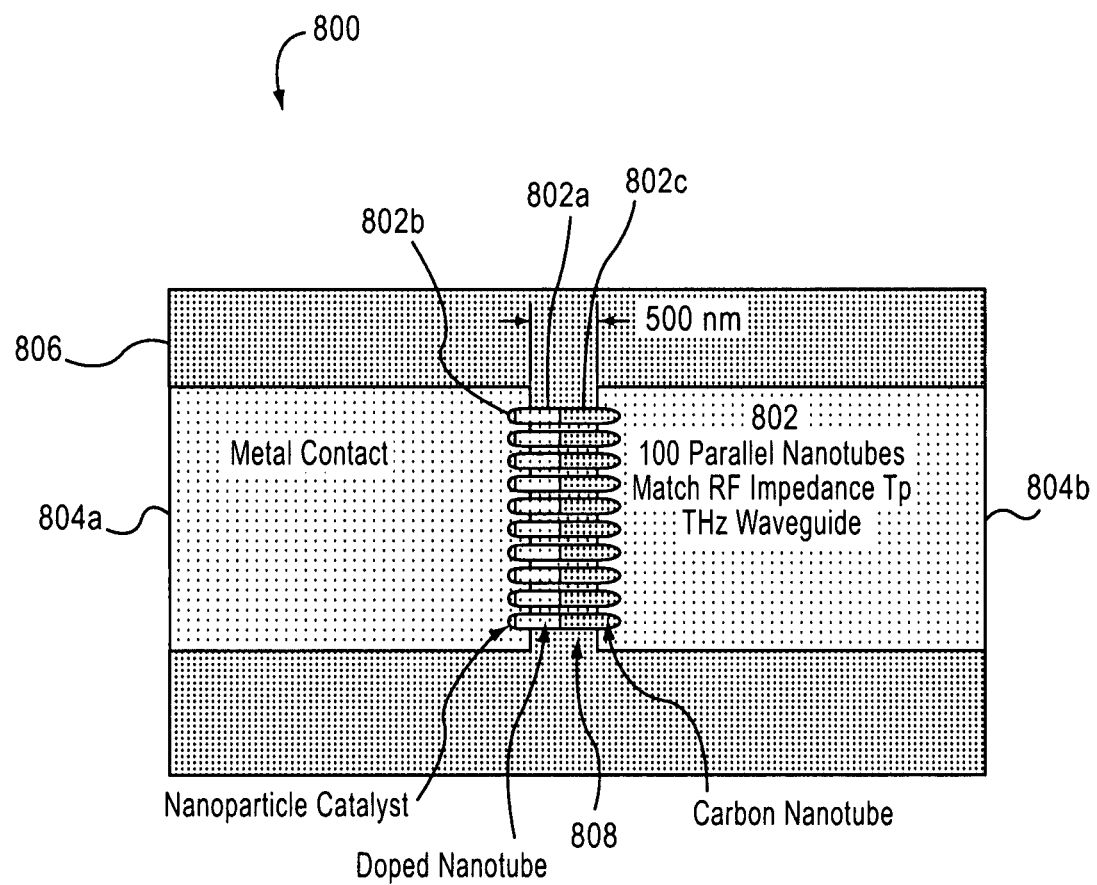
FIG. 8 is a diagram of a diode formed with an array of carbon nanotubes

Referring to FIG. 8, a diode 800 may include an array of doped nanotubes 802 that span a gap 808 between two metal contacts (electrodes) 804a, b, formed on a substrate 806. The metals can have different work functions. Each nanotube in the array 802 can include a doped portion 802a, a catalyst 802b and an undoped portion 802c. The array preferably includes enough nanotubes to form a diode with the proper impedance. It has been found that about 100 nanotubes is appropriate for THz circuits. Metal contacts can be formed before or after CNT growth. It is important to note that the catalyst is not necessary for the diode to function—it is just a byproduct of the growth process.

The low capacitance of CNT p-n junctions, combined with a resistance of about 6.5 kΩ, enables CNT diodes like the one shown in FIG. 8, to operate at frequencies in the Terahertz (THz) range—currently up to about 25 THz. Further, CNT p-n diodes can be turned-ON with a low turn-on current in the range of 7-8 nA. This low turn-on current translates into low local oscillator (LO) power requirements. As a result, CNT diode based mixers can operate on as low as 2 nW of LO power.

The low turn-on current also means very little detectable Shot noise and low flicker noise at room temperature. For example, a CNT diode based mixer fabricated with about 800 individual nanotubes will require about 200 nW of LO (Local Oscillator) power, which is about 37 dB less than conventional Schottky diode based mixers. Flicker noise (1/f noise) is only significant at frequencies below 10 kHz. This means that the primary noise source is thermal noise. Lack of Shot noise and low flicker noise means that the noise temperature of a CNT diode approaches the operating temperature. The CNT diode based mixers can operate in THz frequencies with a noise temperature of about 600 K, which is highly sensitive, compared to the 5,000 K noise temperature of Schottky diode mixers (for conventional Schottky diode mixers, not CNT based Schottky diode mixers). Thus, CNT based receivers can approach the performance of the best cryogenic systems while operating at room temperature.

Aligned nanotubes may be grown up to several mm in length by a unique "fast heating" chemical vapor deposition (CVD) method. See, for example, Huang, S., et al., "Growth of Millimeter-long and horizontally Aligned Single Walled Carbon Nanotubes on Flat Sutstrates," *J. Am. Chem. Soc.* (2003), 125, 5636-37, the contents of which are hereby incorporated by reference.

SWNTs can be grown from a catalyst defined on metal contact pads. The pads can be shaped by e-beam lithography and connected to macroscopic photolithographically defined coupling structures and electrodes. The alignment of the nanotubes can be controlled by the CVD gas flow direction and/or the electric field direction. The SWNT length can be grown to be less than ~700 nm, which is the ballistic length of a CNT, and the contact pads may have minimum feature sizes 250 nm.

The alignment criterion for a single nanotube in a diode array is that it should grow over the second pad so that contact can be made. The major alignment criterion for nanotube arrays is that they remain separate, i.e., do not contact or cross over adjacent nanotubes. Bent nanotubes are not expected since the nanotubes are short in length, but misorientation can result from gas turbulence, electric field fringing effects, or other factors. The tolerable misalignment and/or bending will depend on the spacing between the nanotubes.

Figure 9A:
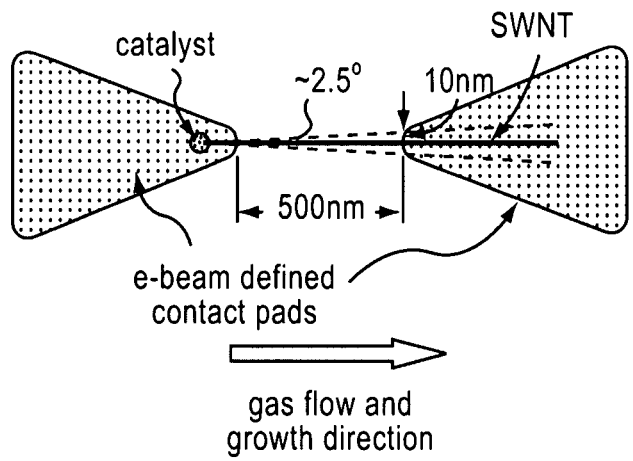
FIGS. 9a-c are illustrations of carbon nanotubes grown across a gap to form a diode.
Figure 9B:
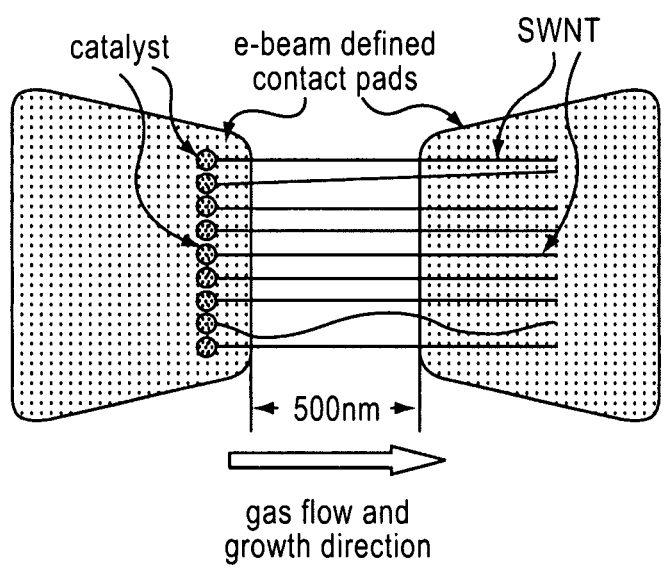
Figure 9C:
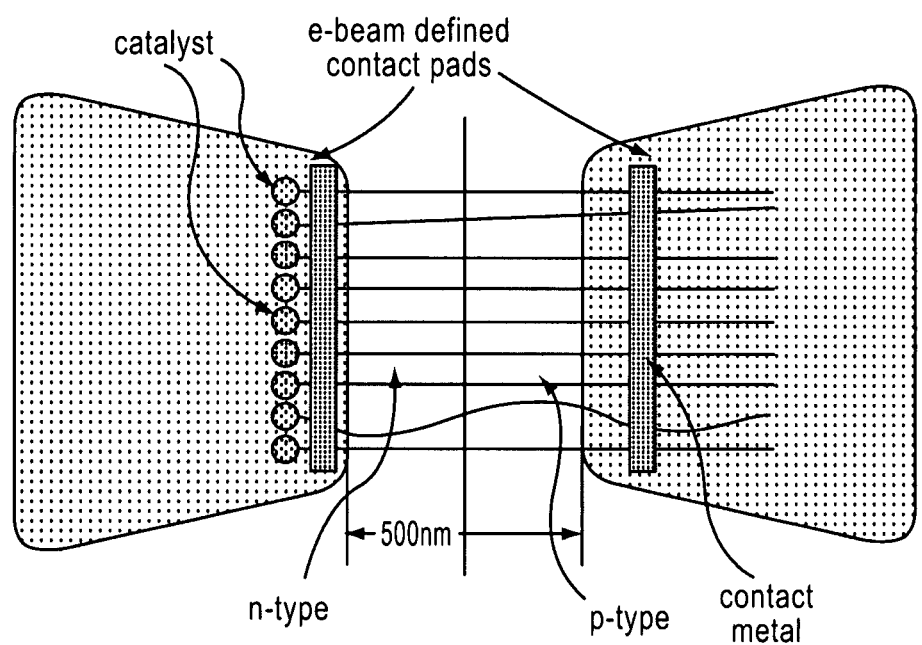

In the example shown in FIGS. 9a-9c, a 500 nm length of free nanotube is shown and has a deviation in alignment of ±2.5° that would be tolerable. Rounding of the contact pad corners at a larger radius would allow for larger alignment deviations, however at the expense of increased capacitance between the two contact pads. By utilizing the technique, RF devices may be manufactured and such devices are described in further detail below.

Figure 1A:
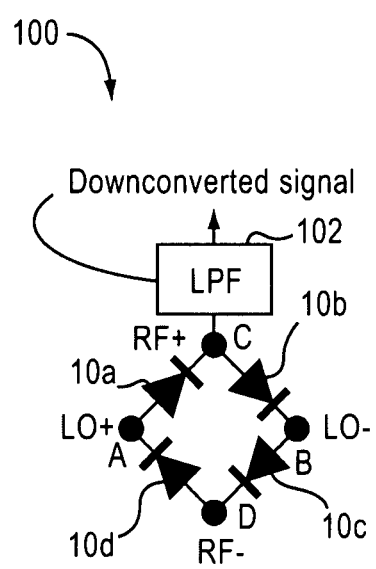
FIG. 1a is a diagram of a four diode quad arrangement for a downconverter.
Figure 1B:
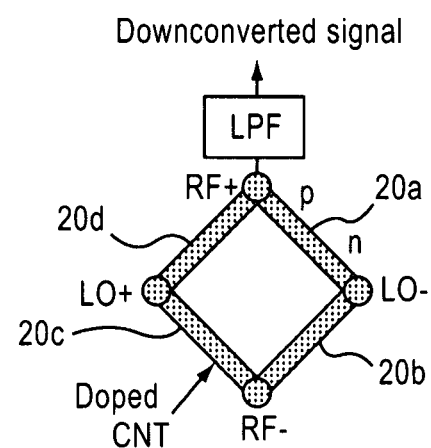
FIG. 1b is a diagram of a downconverter utilizing carbon nanotubes according to an embodiment of the present invention.

Referring to FIG. 1a, a conventional diode quad for a downconverter 100 is shown. Four diodes 10a-10d, typically Schottky diodes, comprise the diode quad in a standard double balanced mixer. A local oscillator (LO) signal (not shown) is input into nodes A and B to switch ("pump") the diodes ON and OFF. A RF signal is input into nodes C and D, which is output to a Low Pass Filter (LPF) 102 as a downconverted signal. LPF 102 is preferably set to cut-out frequencies for translating microwave-optical frequencies to RF. Thus, the LPF 102 may be set at 10-20 GHz Referring to FIG. 1b, a diode quad can be fabricated with the nanotube technology described above. First, four carbon nanotube diodes 20a-d may be grown in an orientation to form the structure similar to the diode quad of FIG. 1a. For example, referring to FIG. 10, crossed nanotubes 1000a, 1000b were grown on successive chemical vapor depositions. The nanotubes 1000a, 1000b were laid down as parallel tubes when the source gases were turned off and the substrate temperature was reduced. The electrodes of a diode quad for a downconverter can be defined on the structure shown in FIG. 10, using electron beam (e-beam) lithography, for example, or by etching. The CNTs may be doped as described above to form the p-n junctions as shown in FIG. 1b.

Figure 2A:
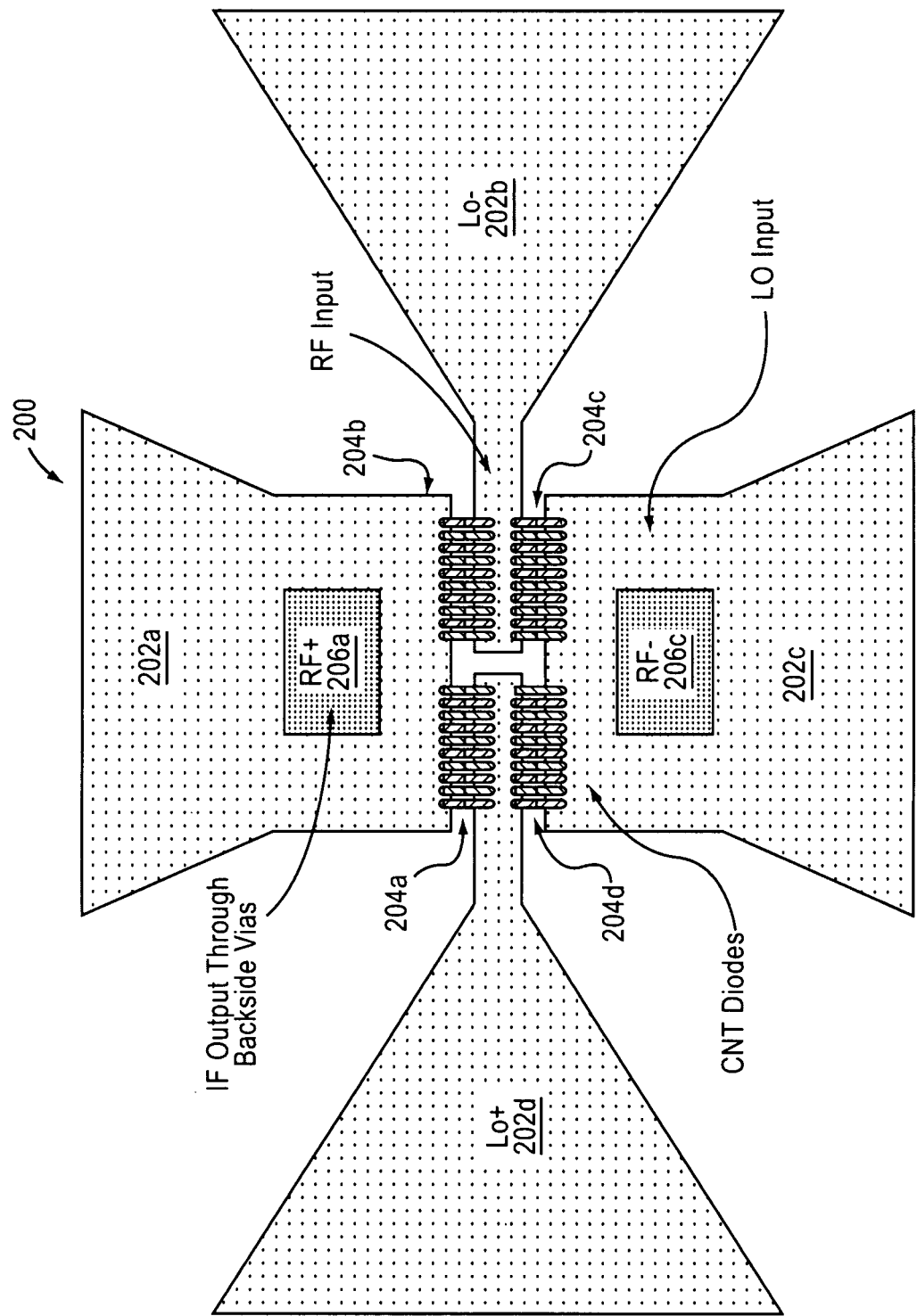
FIGS. 2A-D are diagrams (layout and schematic) of CNT mixers according to embodiments of the present invention.
Figure 2B:
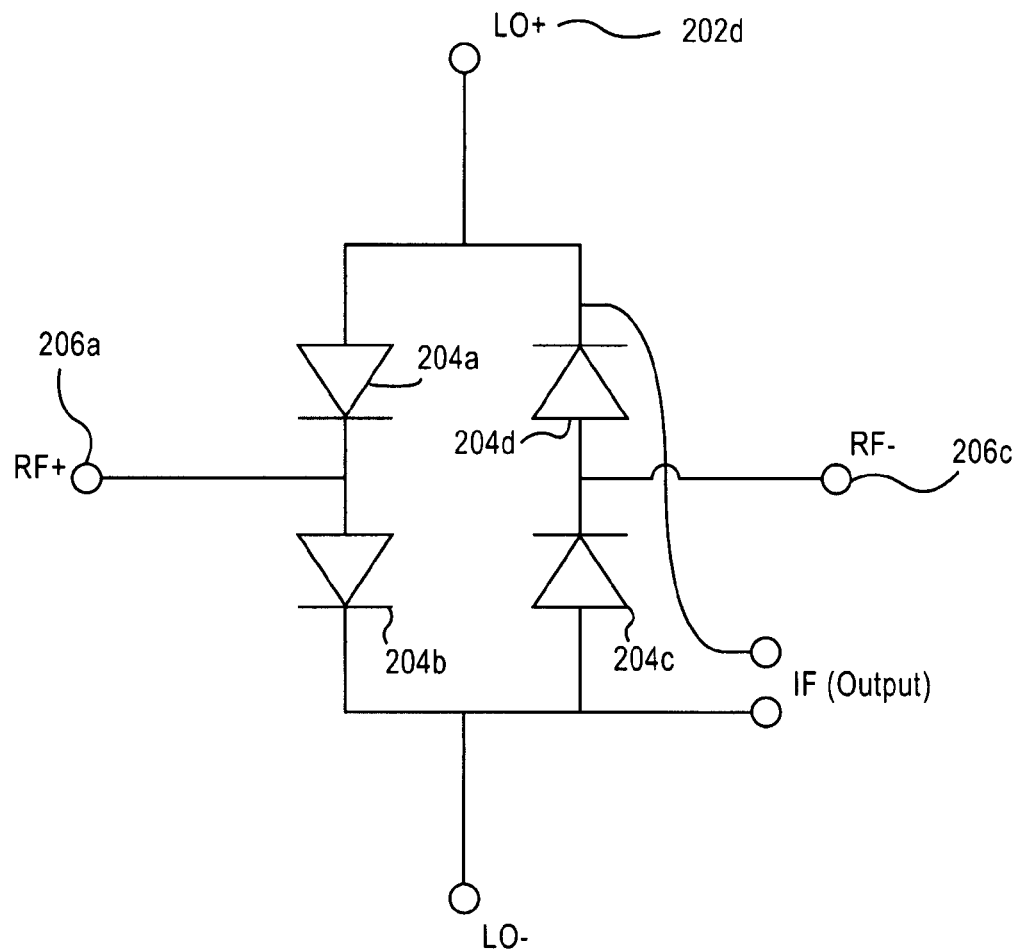

FIG. 2A illustrates the layout of a CNT mixer using CNT array diodes according to an embodiment of the present invention. Electrodes 202a-d can be formed on the surface of a substrate 210 and doped, p-n CNT arrays 204a-d are grown over gaps between the electrodes 202a-d. Alternatively, the CNTs can be grown first and the electrodes deposited on top of them. Electrodes 202b and 202d may be used as inputs for the local oscillator (not shown) and vias 206a and 206c may be provided on electrodes 202a and 202c for IF output. The mixer is shown schematically in FIG. 2B. The resulting mixer can operate at room temperature while achieving a noise temperature of 1000 K, which approaches the performance of the best cryogenic devices.

This structure has the advantage that all CNTs are aligned in the same direction so only one growth step is necessary. The IF output can be taken through backside vias as shown or through an additional wiring level.

It has been demonstrated that CNTs can be used to make field effect transistors (FETs). Recent measurements of CNT FETs indicate that CNTs have the highest mobility of any known semiconductor. CNT FETs have been built with an extrapolated $f_T$ of 1-2 THz. However, the theoretical limit is closer to 10 THz. CNT FETs have a problem with low transconductance, which requires the use of an array of nanotubes.

Figure 2C:
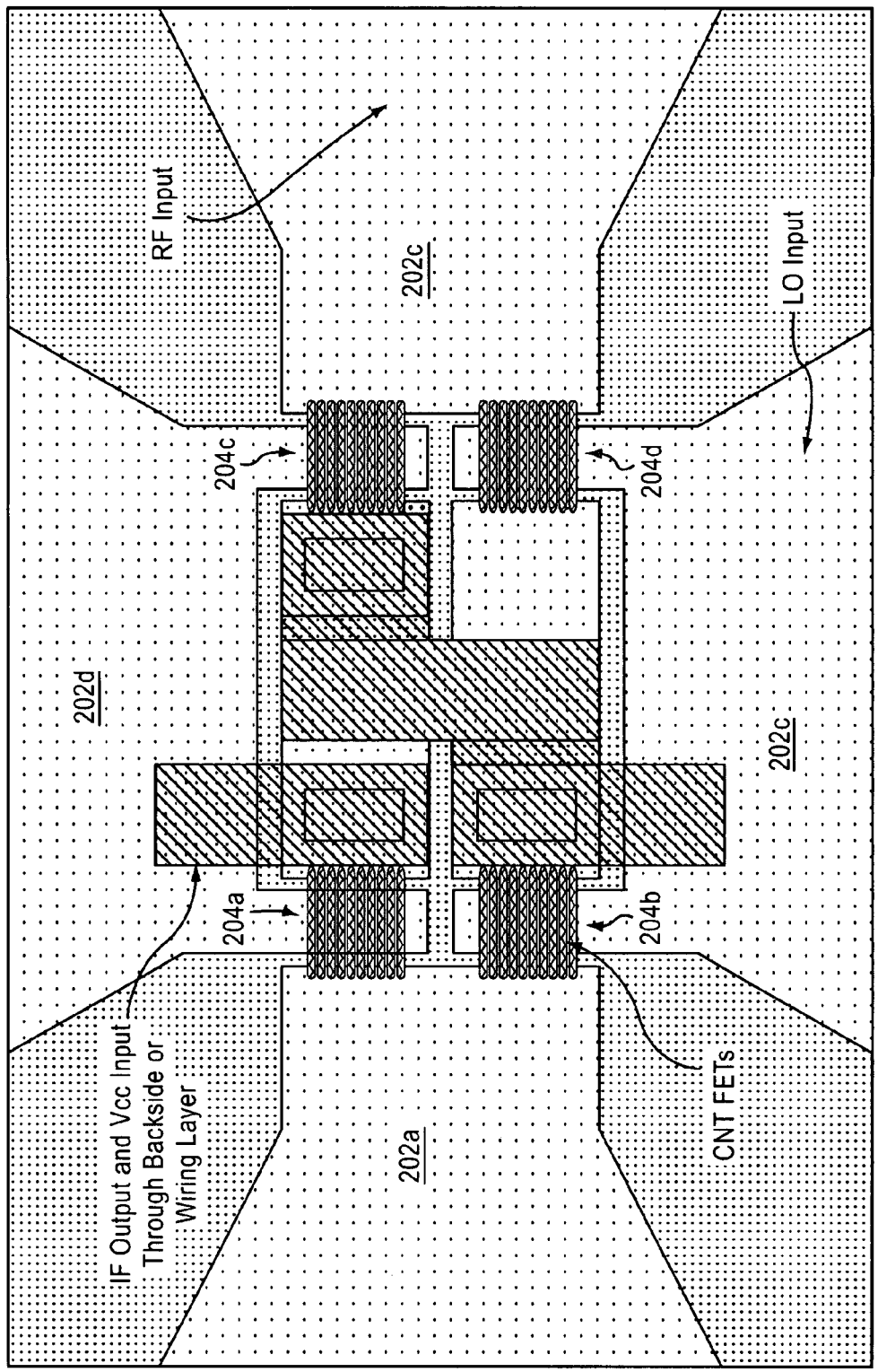
Figure 2D:
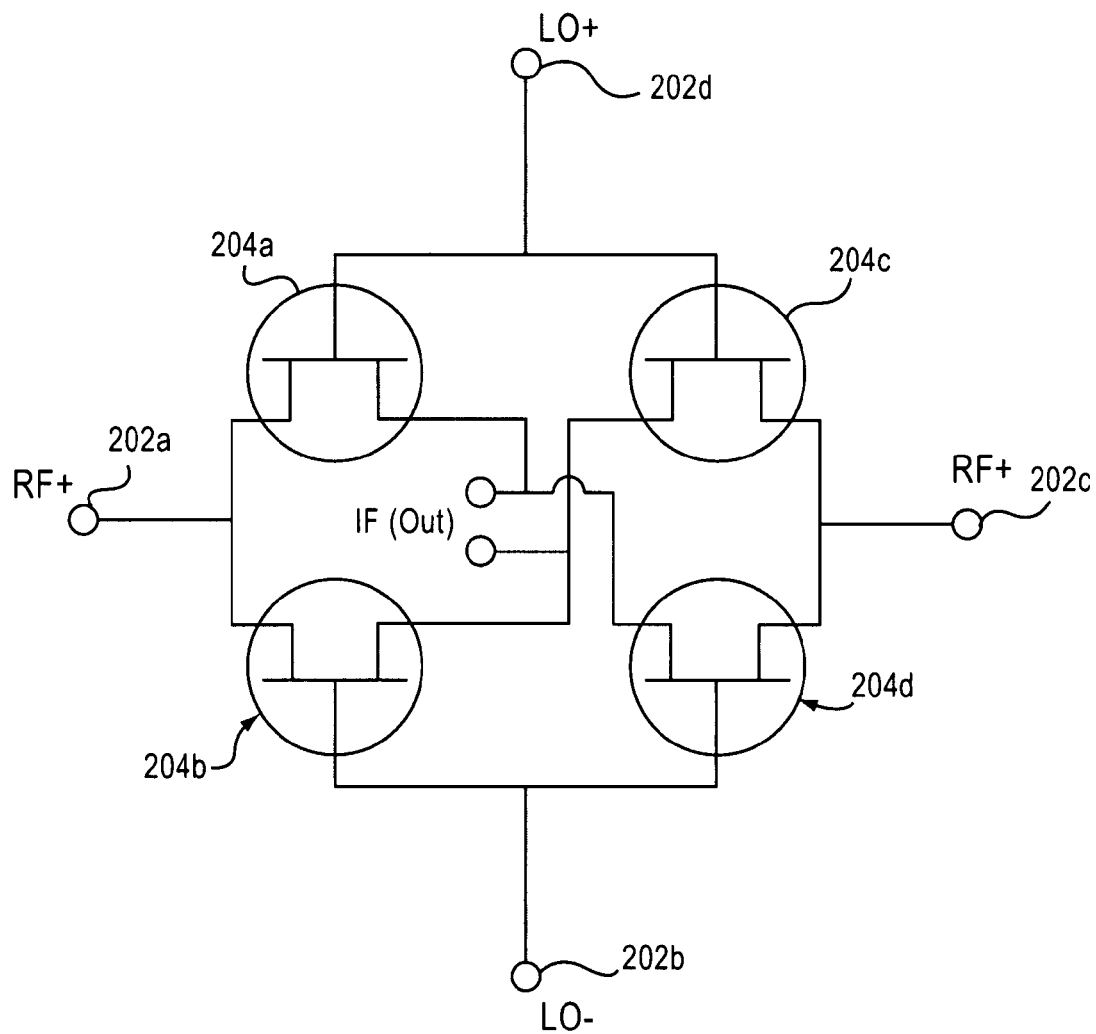

FIG. 2C illustrates a layout of a CNT FET mixer according to an embodiment of the present invention. This mixer uses FETs in place of diodes. IF input is through vias and Vcc input can be made through backside or a wiring layer. The mixer is schematically illustrated in FIG. 2D. The resulting FET mixer can provide an additional 10-20 dB reduction in LO power, but will typically only operate to about 6 THz.

Figure 16:
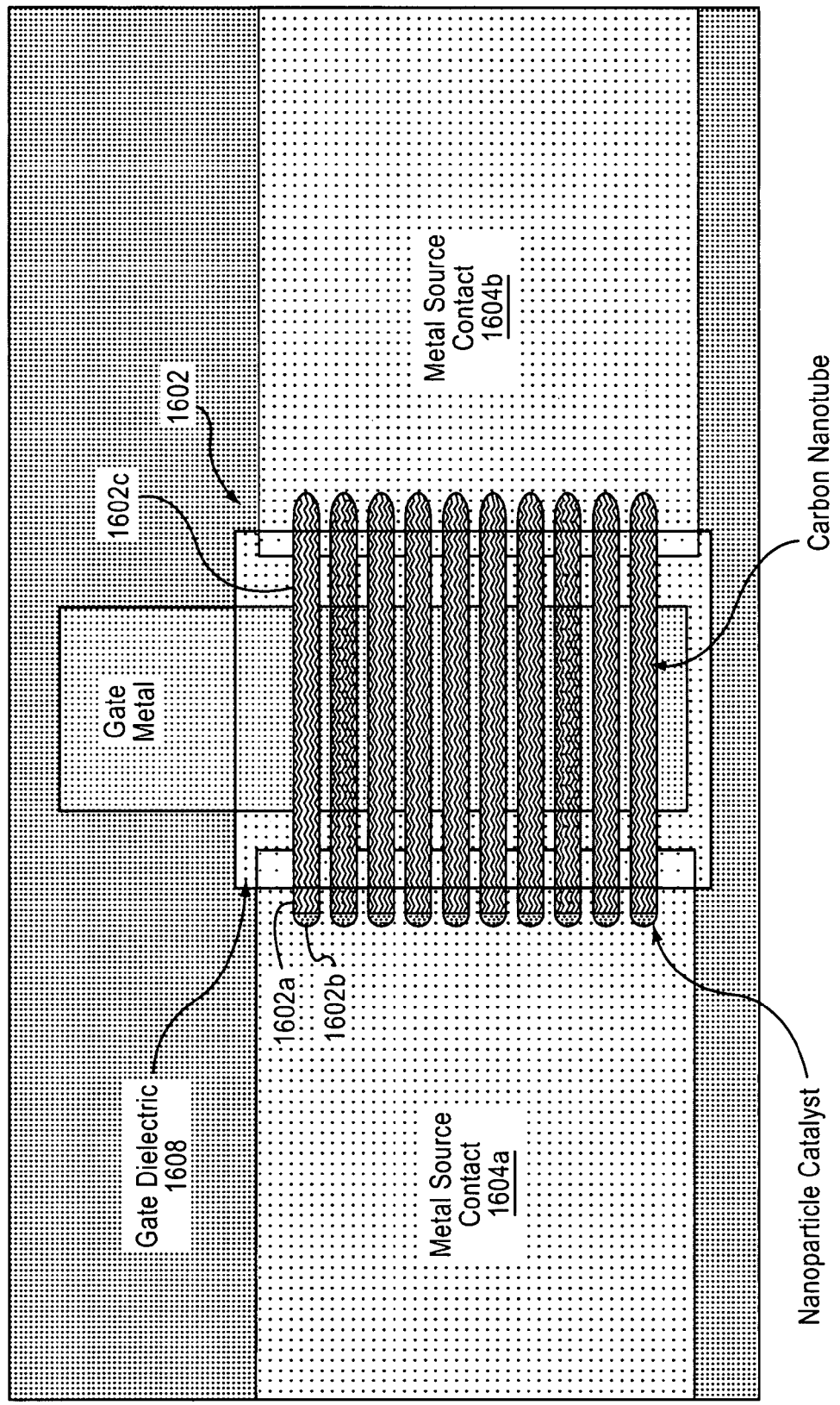
FIG. 16 illustrates the layout of a CNT FET according to an embodiment of the present invention.

An exemplary individual FET layout is shown in FIG. 16. For convenience, the schematic does not include the DC biases necessary to power the CNT FETs. As shown, similar to the diode, an FET includes an array of doped nanotubes 1602 that span a gap 1608 between two metal contacts (electrodes) 1604a, b, formed on a substrate 806. The gap 1608 can include dielectric material. Each nanotube in the array 1602 includes a doped portion 1602a, a catalyst 1602b and an undoped portion 1602c. Metal contacts can be formed before or after CNT growth. It is important to note that the catalyst is not necessary for the diode to function—it is just a byproduct of the growth process. A metal gate 1610 is provided in the gap 1608 and over the diode array 1602.

The CNT diode mixer has the advantage that it (theoretically) operates at 5× higher frequency than the CNT FET mixer. In addition, the FET mixer is active, meaning that it needs a DC power supply to operate, while the diode mixer is passive and needs no additional power. The advantage of the FET mixer is that is requires up to 100× less LO power than the diode mixer which is a big advantage at these frequencies where the LO signal is difficult to generate.

Nanotubes may be grown longer than 1 micrometer to minimize parasitic capacitance for high-frequency operation without any additional parasitic resistance. Metallic carbon nanotubes are highly polarizable and have low resistance (i.e., highly conductive), which make metallic carbon nanotubes excellent antennas. According to another embodiment of the present invention, metallic carbon nanotubes may be used as antennae inputs to couple with a circuit.

Figure 3:
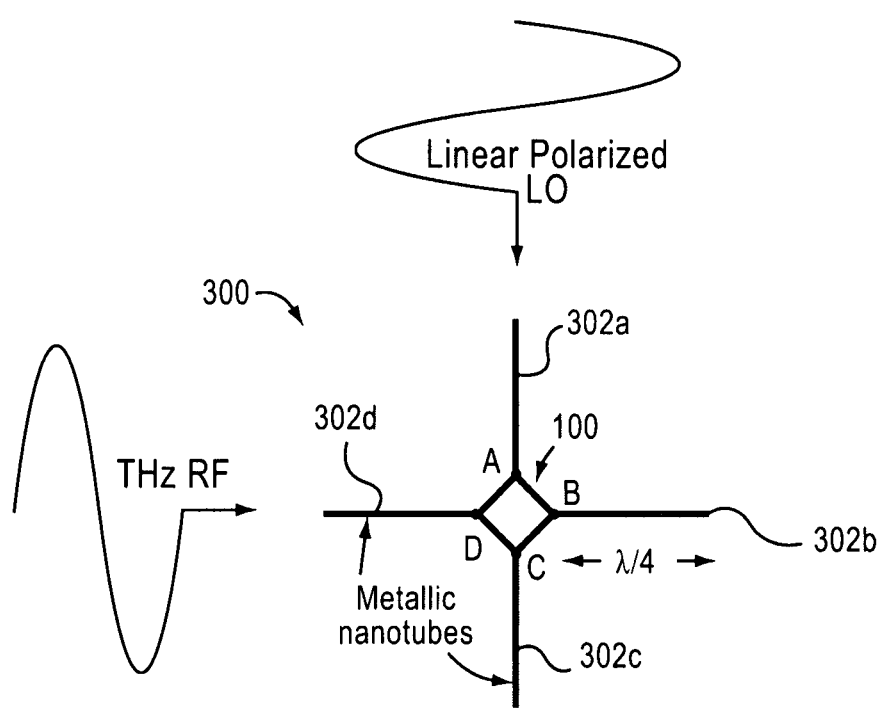
FIG. 3 is a diagram of a quarter-wave antenna utilizing carbon nanotube technology according to an embodiment of the present invention.

Referring to FIG. 3, device 300 includes metallic carbon nanotubes implemented as quarter-wave dipole antennas 302a-d at the corners A-D of a double-balanced diode quad 100, to permit quasi-optic coupling of a radiant local oscillator (LO) to drive the mixer. As shown, a linearly polarized source could illuminate the LO ports, while the RF ports receive the RF signal in the orthogonal polarization.

Figure 5:
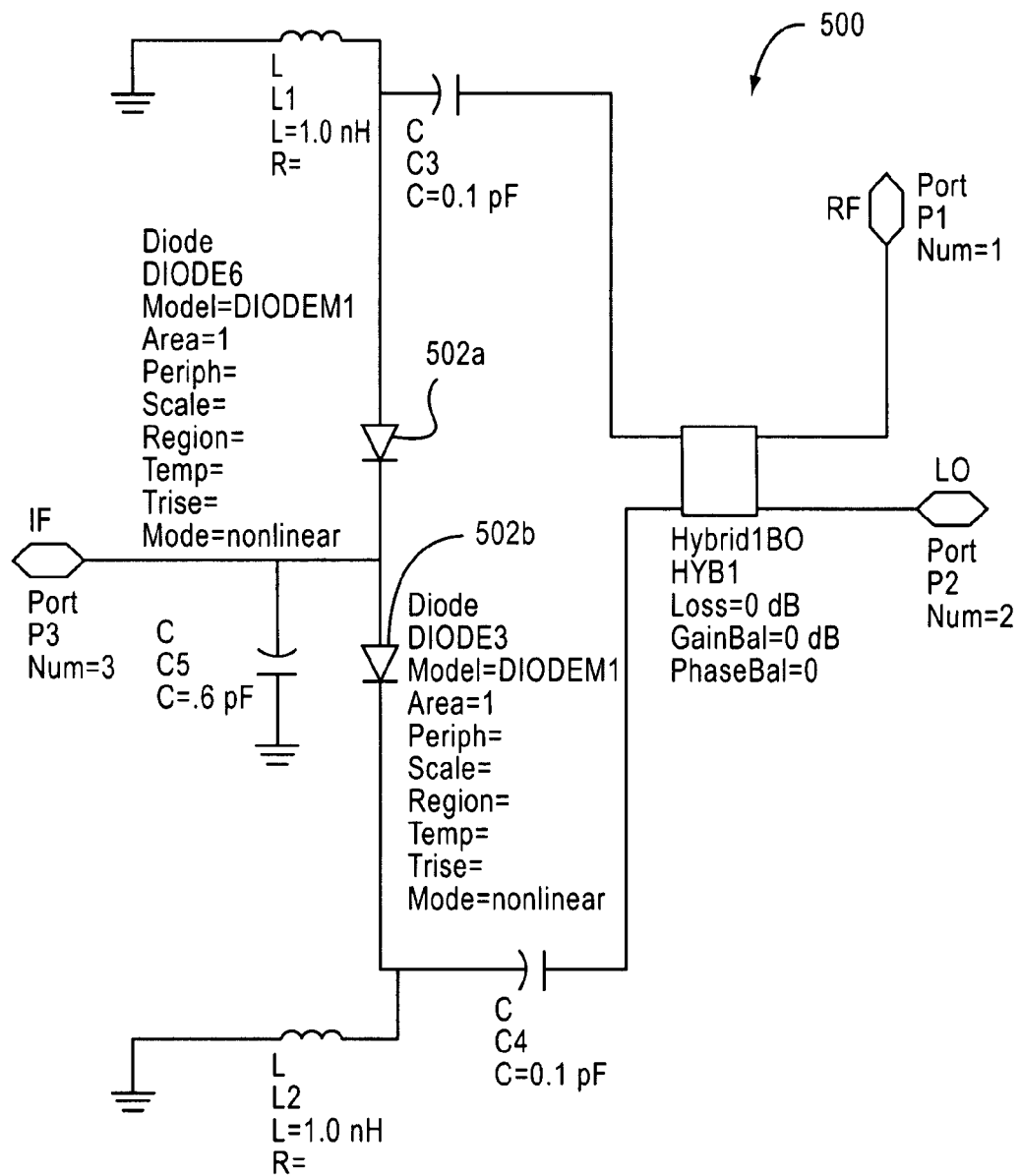
FIG. 5 is a schematic of a balanced mixer.

A schematic of a single balanced mixer 500 is shown in FIG. 5. Like the device of FIG. 3, dipole antenna structures may be used for inputting the RF and LO signals into the mixer 500. Two p-n nanotube diodes 502a and 502b are used to mix the signals to output the downconverted signal as an intermediate frequency (IF) signal.

Single-balanced and double-balanced mixers inherently reject AM noise of the local oscillator used to pump the diodes. As a result, the effective diode noise temperature is lowered, which is critical for millimeter wave mixer applications. The improved sensitivity of CNT detector/downconverters make them very suitable for use in scanning devices and the like, especially for the detection of concealed metal objects. A THz imaging system according to the present invention is capable of imaging through clothing and other materials without the health risks associated with x-ray systems.

Thus, arrays of CNT detector/downconverters may be fabricated utilizing nanotube technology for use in a number of applications, such as for imaging by line scanning, similar to the imaging technique of a fax machine.

Figure 6:
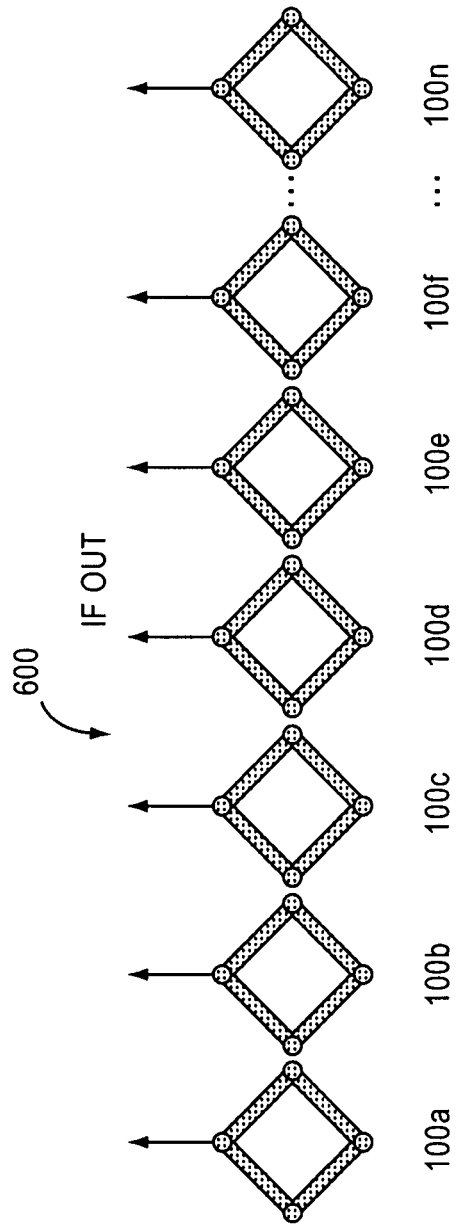
FIG. 6 is a diagram of a linear array detector according to an embodiment of the present invention.

As shown in FIG. 6, a series or array 600 of diode quads 100a-n is fabricated. Optical mirrors could be used to focus an image and scan it across the array 600. Multi-spectral imaging is possible by sweeping the frequency of the LO on successive scans or by using multiple line arrays with different LO's. A collection of mirror gratings could direct the desired LO's onto the various line arrays.

Figure 11:
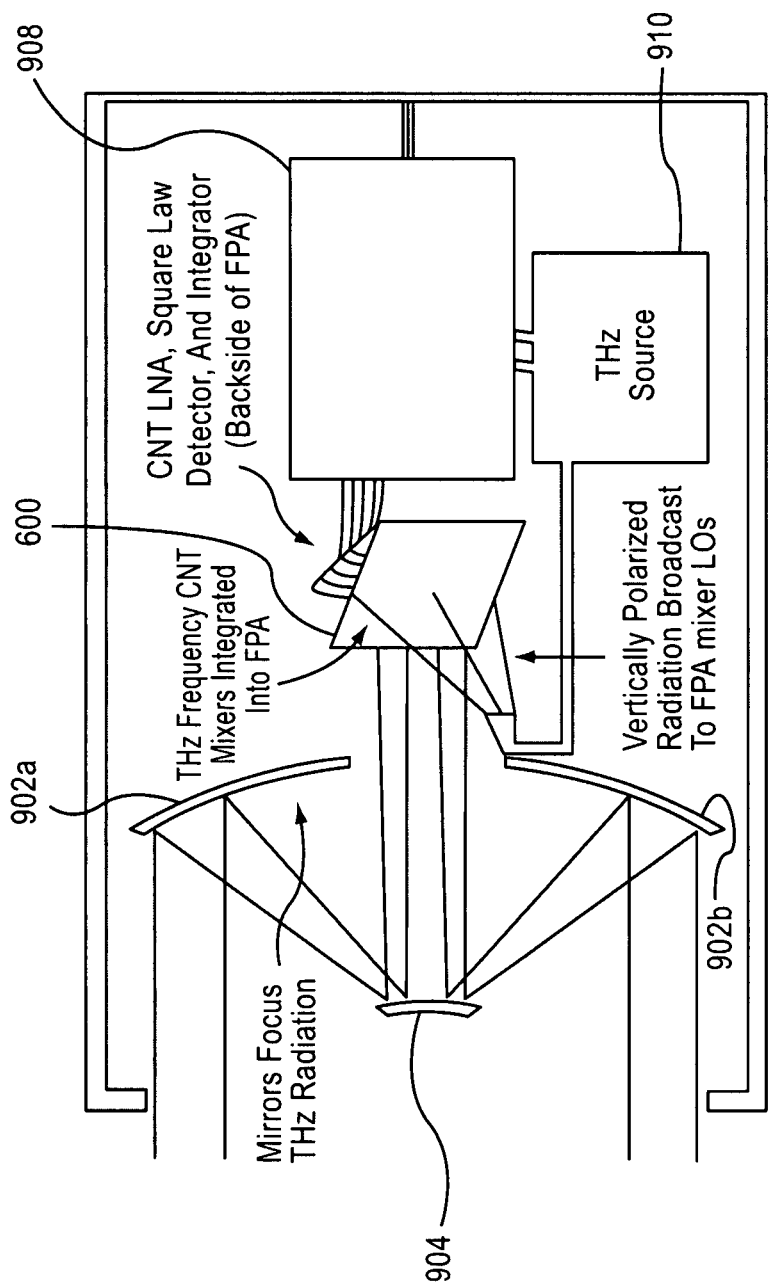
FIG. 11 is a diagram of an imaging device.
Figure 15:
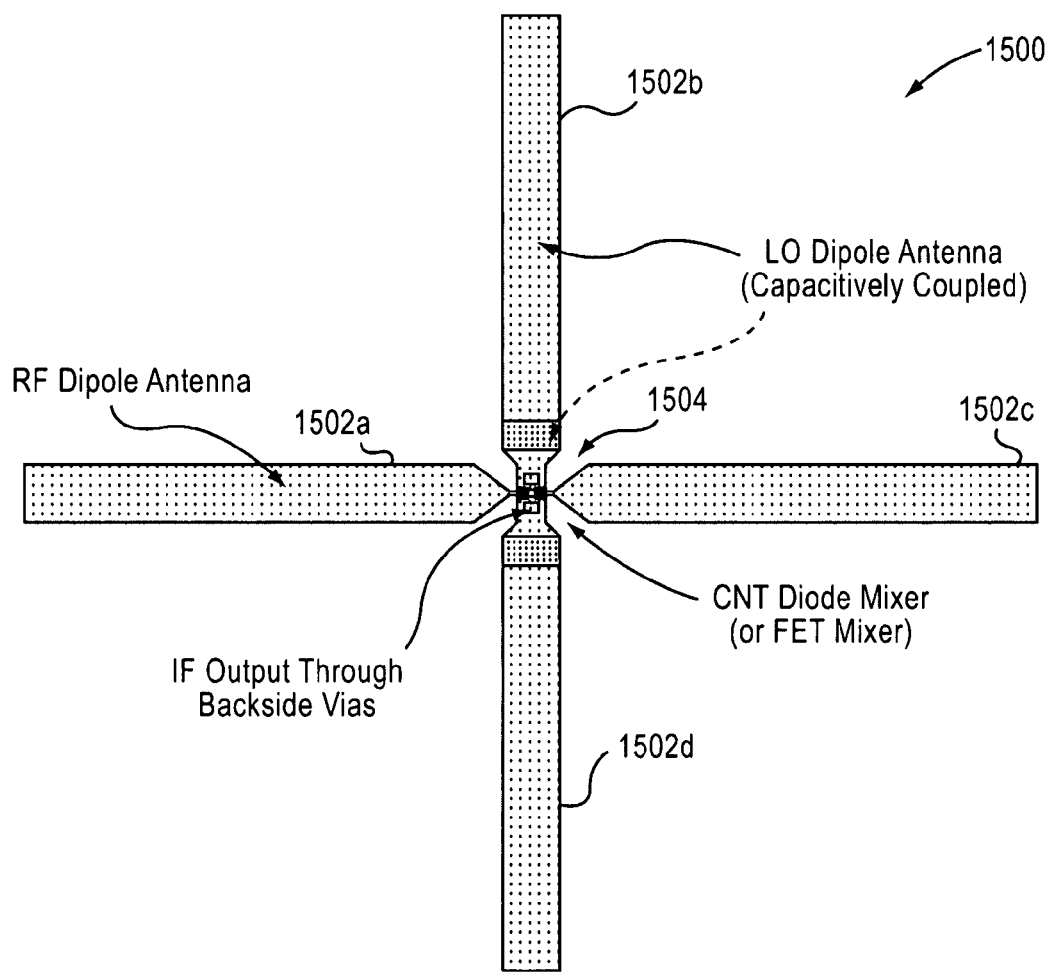
FIG. 15 is an image of an individual pixels of the FPA composed of crossed dipole antennas meeting at a CNT mixer according to an embodiment of the present invention.

The heart of the THz imaging system is the CNT mixer. A CNT based THz imaging system is shown in FIG. 11. A system of mirrors 902a, 902b and 904 can be used to focus the THz frequency radiation (e.g., 5 THz) from source 910, onto the focal plane array (FPA) 600. The mirrors can be used to focus an image and scan it across the array. Diffraction limited focusing of a 2 cm spot at 25 m will require an aperture size of 10", for example. The IF signal outputted is processed by means of circuit 908. The individual pixels of the FPA can be composed of crossed dipole antennas meeting at a CNT mixer as shown in FIG. 15. A vertically polarized LO can be broadcast from a source in front of the FPA.

An individual pixel of the imaging system will be generated from a single CNT mixer, dipole antennas, and the antenna coupling structures. A vertically polarized LO signal will be broadcast to the FPA 600 from a source mounted in front of the array. A horizontal dipole antenna incorporated into the mixer design can be used to capture the THz signal, while a vertical dipole antenna will capture the LO signal. The downconverted 50 GHz IF signal will be removed from the backside of the FPA 600 amplified, detected, digitized, and processed by circuit 908, shown in more detail in FIG. 4.

The detection chain can be built on-chip using CNT electronics or off chip using COTS technology. The integrated signal can pass through an analog MUX to be measured by an ADC. The digital signal can be processed and displayed on an LCD display or the like.

Figure 4:
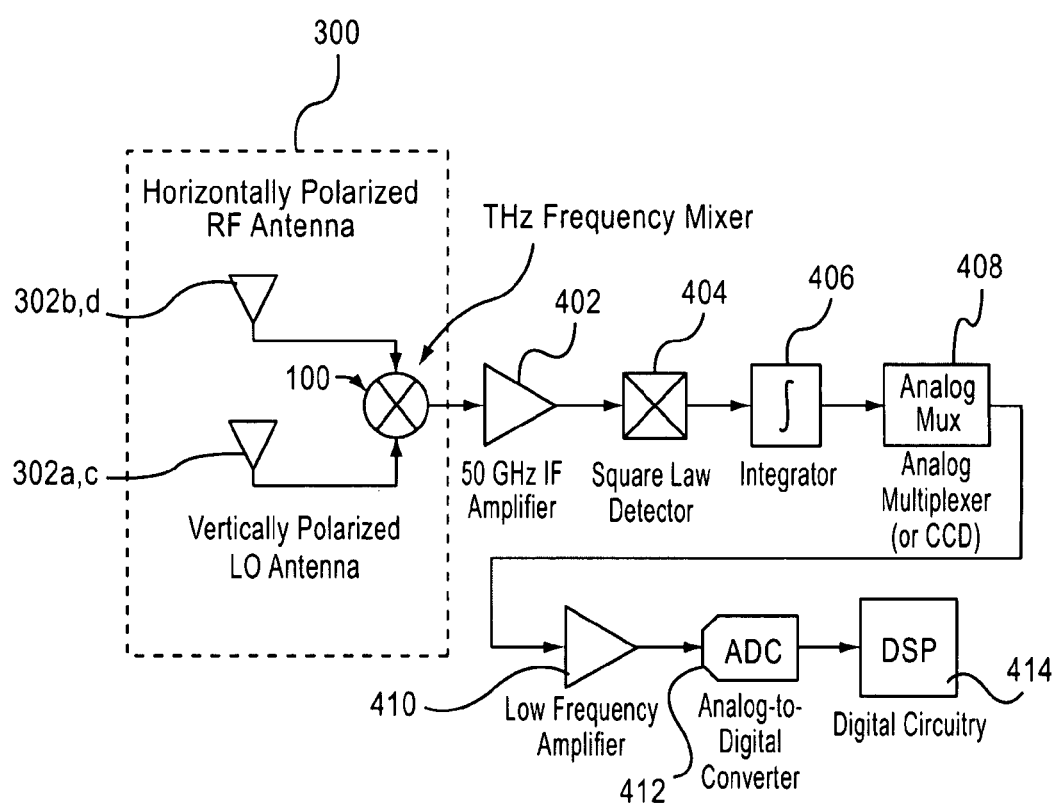
FIG. 4 is a schematic of a pixel processing circuit.

Referring to FIG. 4, the mixer 300 is shown integrated into a pixel chain. The mixer 300 inputs into a IF amplifier coupled with a square law detector 404, an integrator 406, an analog multiplexer 408, a LF amplifier 410, an ND converter 412, which inputs into digital circuitry 414, which may then construct the image or otherwise process the pixel data.

The primary noise sources for the system will be the THz frequency mixer and the IF amplifier. The CNT diode based mixer will have a noise temperature of about 600 K and a conversion loss of at most 10 dB. Assuming a noise figure of 4 dB for the IF amplifier, the input referred system noise temperature will be about 15,000 K. With an input referred noise temperature of 15,000K, the system will be capable of resolving temperature differences of 1K with a 10 ms integration time. This is highly sensitive and will make the device suitable for use in scanning luggage, people, etc., such as for airport security or the like.

The low noise amplifier, square law detector, and integrator can be built on chip using CNT electronics or off-chip using COTS technology.

Figure 12:
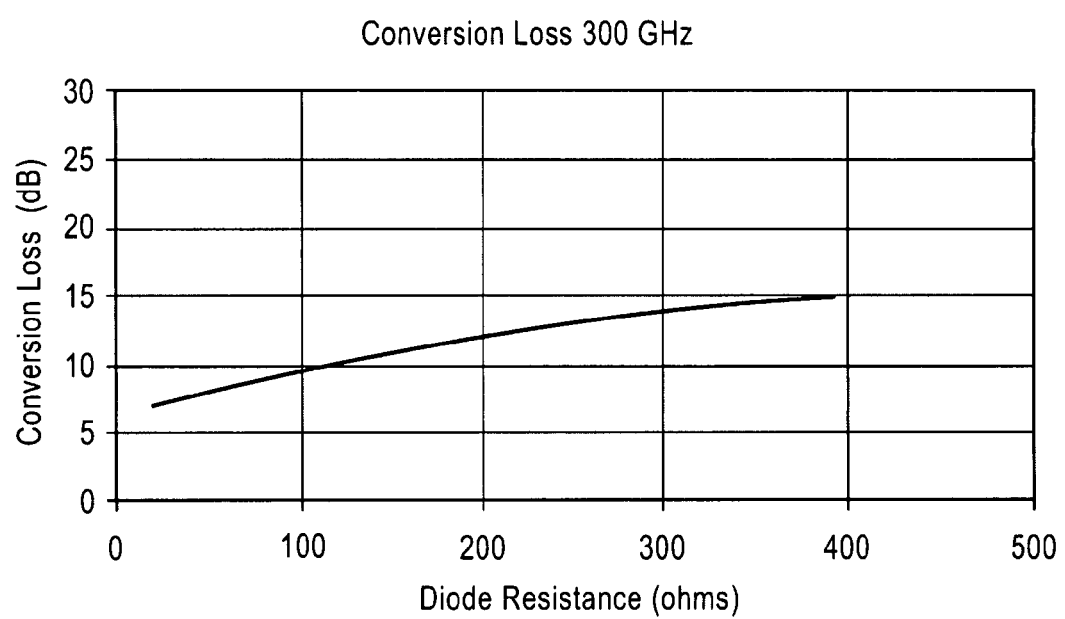
FIGS. 12-13 are graphs of diode conversion loss.
Figure 13:
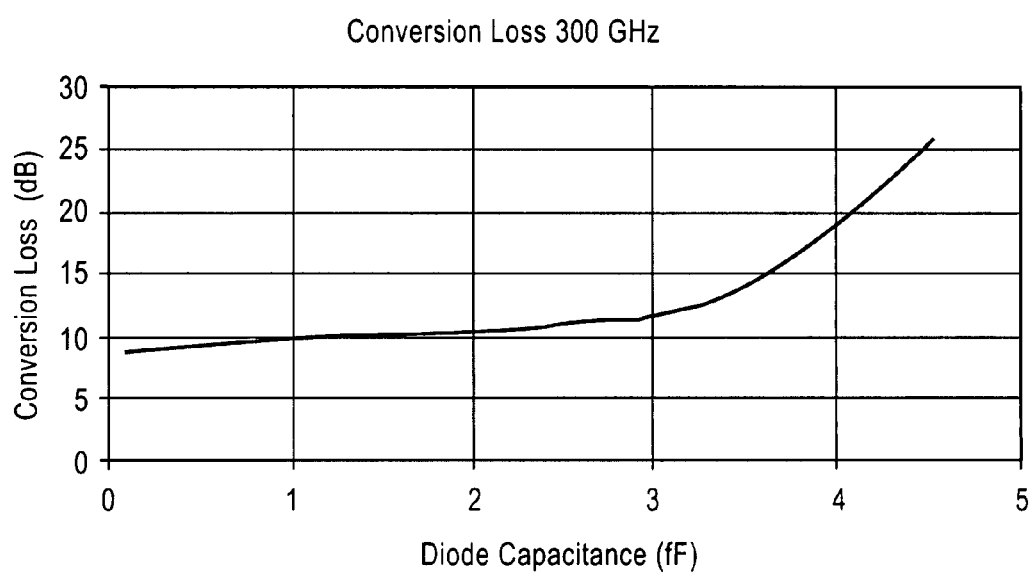

FIG. 12 shows conversion loss versus the diode resistance, and FIG. 13 shows conversion loss versus diode capacitance, for a doped carbon nanotube. At millimeter wave frequency, the diode capacitance needs to be small for optimum performance. Due to extremely small junction area of a carbon nanotube diode, the capacitance will be extremely small. The diode resistance can be decreased by putting multiple junctions in parallel, and by optimizing the junction for low parasitic resistance. Since the nanotube junction is only one atom in thickness, there should be virtually no recombination across the junction, which should lower the diode resistance.

FIG. 15 is a diagram of an individual pixel of the FPA composed of crossed dipole antennas meeting at a CNT mixer according to an embodiment of the present invention. Similar to the device of FIG. 3, dipole antennae 1502a-d are coupled with a CNT mixer. Preferably, the LO Dipole antennae 1502b, d are capacitively coupled to the mixer.

Although embodiments of the present invention include designs to downconvet to base-band, CNT mixers need not mix down to base-band to operate. They could mix down to any output frequency, e.g., the 2 GHz bandwidth from 10 to 12 GHz.

Thus, a number of preferred embodiments have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

The following references provide additional information regarding carbon nanotubes and RF devices and the entire contents of which are hereby incorporated by reference:

H. W. C. Postma, T. Teepen, Z. Yao, M. Grifoni, and C. Dekker, Carbon Nanotube Single-Electron Transistors at Room Temperature, Science (2001), 293, p. 76;

P. E. Roche, M. Kociak, M. Ferrier, S. Gueron, A. Kasumov, B. Reulet, and H. Bouchiat, Shote Notice in Carbon Nanotubes, Proceedings of SPIE (2003), 5115, p. 104;

S. A. Mass, Microwave Mixers, (Boton: Archer House, 1993), p. 135-142;

M. I. Skolnik, The Radar Handbook, (New York, McGraw-Hill, 1970), p. 39-1-39-36;

B. Nabet, et al., "Local Variation of Metal-Semiconducting Carbon Nanotube Contact Barrier Height," Proceedings of the 2002 $2^{nd}$ IEEE Conference on Nanotechnology, 26-28 Aug. 2002, Pages 435-438;

A. S. Vedeneev et al "Molecular-scale rectifying diodes based on Y-junction carbon nanotubes," 1999 International Electron Devices Meeting, IEDM Technical Digest, 5-8 Dec. 1999, Pages 231-233;

P. H. Siegel, "Terahertz Technology," IEEE Trans MTT-50, 910-28, 2002;

Ph. Avouris et al., "Carbon Nanotube Electronics," IEEE Proc. 91, 1772-84, 2003;

P. J. Burke, "Luttinger Liquid Theory as a Model of the Gigahertz Electrical Properties of Carbon Nanotubes," IEEE Trans on Nanotechnology, 1, 129-44, 2002;

I. Mehdi et al, "600 GHJz planar-Schottky-diode subharmonic waveguide mixers," IEEE MIT-S Int. Microwave Symp., San Francisco, Calif., 1996, Paper TU4-E3;

M. S. Shur and J-Q. Lu, "Terahertz Sources and Detectors Using Two-Dimensional Electronic Fluid in High Electron-Mobility Transistors," IEEE Trans. MIT-48, 750-6, 2000;

A. Rahman et al., "Theory of Ballistic Nanotransistors," IEEE Trans. ED-50, 1853-64, 2000;

A. Raychowdhury, S. Mukhopadhyay, K. Roy "Circuit-compatible modeling of carbon nanotube FETS in the ballistic limit of performance," IEEE-NANO 2003, Third IEEE Conference on Nanotechnology, Volume 1, 12-14 Aug. 2003, Pages 343k0346. Nanotechnology;

T. Durkop, S. A. Getty, Enrique Cobas, and M. S. Fuhrer, "Extraordinary mobility in semiconducting carbon nanotubes," Nano Letters, vol. 4, no. 1, pp. 35-39, 2004;

S. Rosenblatt, Y. Yaish, J. Park, J. Gore, V. Sazonova, and P. L. McEuen, "High Performance Electrolyte Gated Carbon Nanotube Transistors," Nano Letters, vol. 2, no. 8, pp. 869-872, 2002;

Bethune, D. S.; Kiang, C. H.; DeVries, M. S.; Gorman, G.; Savoy, R.; Beyers, R. Cobalt-catalysed growth of carbon nanotubes with single-atomic-layer walls, Nature (1993), 363, 605;

Journet, C.; Maser, W. K.; Bernier, P.; Loiseau, A; Cahpelle, M. L. d. 1.; Lefrant, S.; Deniard, P.; Lee, R.; Fischer, J. E. Large-scale production of single-walled carbon nanotubes by the electric-arc technique, Nature (1997), 388, 756;

Thess, A.; Lee, R.; Nikolaev, P.; Dai, H.; Petit, P.; Robert, J.; Xu, C.; Lee, Y. H.; Kim, S. G.; Rinzler, A. G.; Colbert, D. T.; Scuseria, G. E.; Tomanek, D.; Fischer, J. E.; Smalley, R. E. Crystalline Ropes of Metallic Carbon Nanotubes, Science (1996), 273, 483;

Zhang, Y. G.; Chang, A. L.; Cao, J.; Wang, Q.; Kim, W.; Li, Y. M.; Morris, N.; Yenilmez, E.; Kong, J.; Dai, H. J. Electric-field-directed growth of aligned single-walled carbon nanotubes, Appl. Phys. Lett. (2001), 79, 3155-3157;

Su, M.; Li, Y.; Maynor, B.; Buldum, A.; Lu, J. P.; Liu, J. Lattice-oriented growth of single-walled carbon nanotubes, J. Phys. Chem. B (2000), 104, 656505-6508;

Franklin, N. R.; Dai, H. An Enhanced CVD Approach to Extensive Nanotube Networks with Directionality, Adv. Mater. (2000), 12, 890-894;

Huang, S.; Cai, X.; Liu, J. Growth of Millimeter-long and Horizontally Aligned Single Walled Carbon Nanotubes on Flat Substrates, J. Am. Chem. Soc. (2003), 125, 5636-5637;

Cheung, C. L.; Kurtz, A.; Park, H.; Lieber, C. M. Diameter-controller synthesis of carbon nanotubes, J. Phys. Chem. B (2002), 106, 2429-2433;

Li, Y. M.; Kim, W.; Zhang, Y. G.; Rolandi, M.; Wang, D. W.; Dai, H. J. Growth of single-walled carbon nanotubes from discrete catalytic nanoparticles of various sizes, J. Phys. Chem. B (2001), 105, 11424-11431;

Tang, Z. K.; Sun, H. D.; Wang, J.; Chen, J.; Li, G. Mono-sized single-wall carton nanotubes formed in channels of A1PO4-5 single crystal, Appl. Phys. Lett. (1998), 73, 2287;

An, L.; Owens, J. M.; McNeil, L. E.; Liu, J. Synthesis of nearly uniform single-walled carbon nanotubes using identical metal-containing molecular nanoclusters as catalysts, J. Am. Chem. Soc. (2002), 124, 13688-13689;

P. Collins, M. Arnold and Ph. Avouris, Science 292, 706 (2001);

P. McEuen, "Single-Walled Carbon Nanotube Electronics," IEEE Trans. Nanotech., I, 78 (2002);

H. Soh, C. Quate, A. Motpurgo, C. Marcos, J. Kong, and H. Dai, Appl. Phys. Lett. 75, 627 (1999);

N. Franklin, Q. Wang, T. Tomblor, A. Javey, M. Shim, H. Dai, Appl. Phys. Len. 81, 913 (2002);

C. Cheung, A. Kurtz, H. Park, C. Lieber, "Diameter-controlled synthesis of carbon nanotubes," J. Phys. Chem. 106, 2429 (2002);

R. S. Lee, J. J. Kim, J. E. Fischer, A. Thess, R. Smalley, "Conductivity enhancement in single-walled carbon nanotube bundles doped with K and Br," Nature, 388, 255 (1997);

M. Bockrath, J. Hone, A. Zenl, P. McEuen, A. Rinzler, R. Smalley, Phys. Rev. B, 61, R10606 (2000);

J. Kong, H. Dai, "Full and Modulated Chemical Gating of Individual CNTs by Organic Amine Compounds," J. Phys. Chem B. 105, 2890 (2001).

V. Derycke, R. Martel, J. Appenzeller, Ph. Avouris, Nano Letters, 1, 453 (2001);

C. Zhou, J. Kong, E. Yenilmez, H Dai, Science, 290, 1552 (2000).

P. H. Siegel, "THz Technology," IEEE Transactions on Microwave Theory and Techniques, Vol. 50 (3), pp. 910-928, March 2002;

D. T. Young and J. C. Irwin, "Millimeter frequency conversion using Au-n-type GaAs Schottky barrier epitaxial diodes with a novel contacting technique," Proc. IEEE, vol. 53, no. 12, pp. 2130-31, December 1965;

M. C. Gaidis, H. M. Pickett, C. D. Smith, R. P. Smith, S. C. Martin and P. H. Siegel "A 2.5 THz Receiver Front-End for Spaceborne Applications," IEEE Transactions Microwave Theory and Techniques, vol. 48, no. 4, pp. 733-739, April 2000;

Mehdi, T. Lee, D. Humphrey, S. Martin, R. J. Dengler, J. E. Oswald, A. Pease, R. P. Smith and P. H. Siegel, "600 GHz Planar-Schottkey-Diode Subharmonic Waveguide Mixers," 1996 IEEE MTT-S Int. Microwave Symposium, San Francisco, Calif., paper TU4-E3, Jun. 17-21, 1996;

S. J. Tans, R. M. Verschueren, C. Dekker, *Nature* 393, 49 (1998).

R. Martel, T. Schmidt, H. R. Shea, T. Hertel, P. Avouris, *Applied Physics Letters* 73, 2447 (1998);

T. Durkop, S. A. Getty, E. Cobas, M. S. Fuhrer, *Nano Letters* 4, 35 (2004);

A. Javey, J. Guo, Q. Wang, M. Lundstrom, H. J. Dai, *Nature* 424, 654 (Aug. 7, 2003);

Y. Yaish et al., published online at http://xxx.lanl.gov/abs/cond-mat0305108) (2003); and D. H. Cobden, M. Bockrath, P. L. McEuen, A. G. Rinzler, R. E. Smalley, *Physical Review Letters* 81, 681 (1998).

We claim:

1. An imaging system, comprising:
   an RF source;
   a focal plane array comprising a plurality of carbon nanotube mixers for capturing RF signals, down-converting said signals to a selected bandwidth, and outputting an output signal; and
   means for focusing an RF signal output from said RF source onto said focal plane array.

2. The imaging system as recited in claim 1, wherein each of said carbon nanotube mixers comprises:
   at least a pair of diodes including first and second carbon nanotube diodes, each carbon nanotube diode including a p-n junction;
   an RF input coupled with each of said diodes; and
   a local oscillator (LO) input coupled with each of said diodes.

3. The imaging system as recited in claim 2, wherein said at least a pair of diodes comprises:
   a substrate;
   first and second electrodes formed on the surface of said substrate and separated by a first gap;
   fourth and third electrodes formed on the surface of the substrate and separated by a second gap, a portion of said fourth and said third electrodes being formed in said first gap;
   a first p-n junction carbon nanotube diode connecting said first electrode with said third electrode;
   a second p-n junction carbon nanotube diode connecting said first electrode with said fourth electrode;
   a third p-n junction carbon nanotube diode connecting said second electrode with said third electrode; and
   a fourth p-n junction carbon nanotube diode connecting said second electrode with said fourth electrode.

4. The imaging system as recited in claim 3, wherein the p-side of said first diode is coupled with the n-side of said second diode, the p-side of said second diode is coupled with the n-side of said third diode, the p-side of said third diode is coupled with the n-side of said fourth diode, and said p-side of said fourth diode is coupled with the n-side of said first diode.

5. The imaging system as recited in claim 2, wherein said RF input comprises at least one metallic carbon nanotube antenna.

6. The imaging system as recited in claim 2, wherein said LO input comprises at least one metallic carbon nanotube antenna.

7. The imaging system as recited in claim 2, wherein said RF source produces a signal having a frequency over 1 THz.

8. The imaging system as recited in claim 1, wherein said means for focusing comprises a plurality of mirrors.

9. The imaging system as recited in claim 1, further comprising processing means for processing an output of said focal plane array to generate an image.

10. The imaging system as recited in claim 9, further comprising a display device coupled with said processing means for displaying said image.

11. The imaging system as recited in claim 1, wherein each said mixer comprises at least four carbon nanotube devices arranged in a diode quad configuration; said RF input being coupled to a first pair of carbon nanotube devices and a local oscillator input being coupled to a second pair of carbon nanotube devices.

12. The imaging system as recited in claim 1, wherein each said mixer comprises a plurality of carbon nanotube field effect transistors (FET).

13. A focal plane array comprising:
   a plurality of carbon nanotube (CNT) capturing RF signals, down-converting said signals to a selected bandwidth, and outputting an output signal;
   wherein each of said CNT mixers comprises:
      a diode quad including first, second, third and fourth carbon nanotube diodes, each carbon nanotube diode including a p-n junction;
      an RF input coupled with each of said diodes; and
      a local oscillator (LO) input coupled with each of said diodes;
   wherein said diode quad comprises:
      a substrate;
      first and second electrodes formed on the surface of said substrate and separated by a first gap;
      fourth and third electrodes formed on the surface of the substrate and separated by a second gap, a portion of said fourth and said third electrodes being formed in said first gap;
      a first p-n junction carbon nanotube diode connecting said first electrode with said third electrode;
      a second p-n junction carbon nanotube diode connecting said first electrode with said fourth electrode;
      a third p-n junction carbon nanotube diode connecting said second electrode with said third electrode; and
      a fourth p-n junction carbon nanotube diode connecting said second electrode with said fourth electrode.

14. The focal plane array as recited in claim 13, wherein the p-side of said first diode is coupled with the n-side of said second diode, the p-side of said second diode is coupled with the n-side of said third diode, the p-side of said third diode is coupled with the n-side of said fourth diode, and said p-side of said fourth diode is coupled with the n-side of said first diode.

15. The focal plane array as recited in claim 14, wherein said LO input comprises at least one metallic carbon nanotube antenna.

16. An imaging method comprising steps of:
   focusing RF signals output from an RF source onto a focal plane array comprising a plurality of carbon nanotube (CNT) mixers for capturing RF signals, down-converting said signals to a selected bandwidth, and outputting an output signal; and processing the output signal from said focal plane array to generate an image.

17. The imaging method as recited in claim 16, wherein each said mixer comprises a plurality of carbon nanotube field effect transistors (FET).

18. The imaging method as recited in claim 16, wherein each said mixer comprises at least four carbon nanotube devices arranged in a diode quad configuration; said RF input being coupled to a first pair of carbon nanotube devices and a local oscillator input being coupled to a second pair of carbon nanotube devices.

* * * * *